United States Patent [19]

Struve et al.

[11] 4,374,776

[45] Feb. 22, 1983

[54] STEROL CONCENTRATES, THE PREPARATION THEREOF, AND THEIR USE IN THE TRANSFORMATION OF STEROLS BY FERMENTATION

[75] Inventors: Alfred Struve, Hilden; Frank F. Hill, Mettmann-Obschwarzbach; Joachim Schindler, Hilden, all of Fed. Rep. of Germany

[73] Assignee: Henkel Kommanditgesellschaft auf Aktien, Düsseldorf-Holthausen, Fed. Rep. of Germany

[21] Appl. No.: 183,622

[22] Filed: Sep. 2, 1980

[30] Foreign Application Priority Data

Sep. 7, 1979 [DE] Fed. Rep. of Germany ....... 2936125

[51] Int. Cl.$^3$ .............................................. C07J 9/00
[52] U.S. Cl. .................................. 260/397.25; 435/55
[58] Field of Search .................................... 260/397.25

[56] References Cited

U.S. PATENT DOCUMENTS 4,124,607  11/1978  Beaton ........................... 260/397.25

Primary Examiner—Elbert L. Roberts
Attorney, Agent, or Firm—Hammond & Littell, Weissenberger and Muserlian

[57] ABSTRACT

This invention relates to a process for the preparation of a concentrate containing sterol compounds of natural origin, which concentrate is suitable as a starting material for the transformation of sterol compounds by fermentation, which comprises the steps of:

(a) transesterifying distillation residues from the processing of natural fats and/or oils with a lower alcohol; and (b) subjecting the product of step (a) to molecular distillation to produce a main fraction having a content of up to about 50 percent by weight of sterol compounds.

The invention also relates to sterol concentrates produced thereby and their transformation to valuable secondary products.

18 Claims, No Drawings

STEROL CONCENTRATES, THE PREPARATION THEREOF, AND THEIR USE IN THE TRANSFORMATION OF STEROLS BY FERMENTATION

FIELD OF THE INVENTION

This invention is directed to novel sterol concentrates. More particularly, this invention is directed to novel sterol concentrates, their preparation from residues of the processing of vegetable and/or animal fats and/or oils, and their use in the transformation of sterols by fermentation into valuable secondary products such as steroid intermediates.

BACKGROUND OF THE INVENTION

There is a growing demand for steroid intermediates for the preparation of pharmaceutically active substances. This demand is increasingly met with cleavage products of sterols obtained by fermentation in aqueous nutrient solution. During such a microbial breakdown the sterols have been used in pure or very highly enriched form. Addition of emulsifying agents provides for a suitable distribution of the sterols in the aqueous nutrient solution. Such additives or accompanying substances in the sterols must induce the desired homogenization of the nutrient medium; however, they must not interfere with the growth of the microorganisms or with the desired breakdown of the sterols.

The preparation of pure sterol compounds of natural origin from vegetable and/or animal oils and/or fats, in which they are present in a low concentration as secondary substances, requires a complex process. According to British Pat. No. 489,623, natural fats or oils are subjected to molecular distillation. This results in a fraction enriched with sterol compounds, from which fraction the sterol can be obtained, if desired, by selective solvents, after saponification of the accompanying substances in the fraction. British Pat. No. 493,948 is also concerned, for example, with the distillation of sterol compounds under high vacuum. Here, the addition of carrier materials that have the same boiling range as the sterol compounds and are co-distilled with them is suggested for the distillation. These carrier materials must be capable of being separated subsequently from the sterol compounds by physical or chemical means.

A similar procedure is described in U.S. Pat. No. 2,146,894. According to the procedure disclosed, carrier materials of diverse origin are used to facilitate the distillation of natural substances with high boiling points under vacuum. Examples of such materials include fatty acids, esters such as aliphatic phthalates, benzyl phthalate, diglycerol tetrapropionate, mineral oil fractions, terpenes, and similar substances. Here, too, provisions are made for the separation of the co-distilled natural substance, and it is not detrimental when limited amounts of the natural substance remain in the carrier material, since this is to be reused.

In U.S. Pat. No. 4,148,810, a process for the isolation of sterols from distillation residues from the processing of fats is described. According to the process, the sterols are separated by transesterification with methanol and then isolated from the transesterification mixture by the formation of the adduct with calcium chloride in a aprotic solvent and with the small addition of a protic solvent.

OBJECTS OF THE INVENTION

It is an object of the invention to provide novel sterol concentrates.

It is also an object of the invention to provide novel sterol concentrates of natural origin and a method for preparing such novel sterol concentrates from processing residues.

It is a further object of the invention to provide a method of using such novel sterol concentrates in the transformation of sterol compounds by fermentation to secondary products such as steroid compounds.

These and other objects of the invention will become more apparent in the description below.

DETAILED DESCRIPTION OF THE INVENTION

Sterols are a group of polycyclic alcohols containing the common steroid nucleus, an 8 to 10 carbon atom side chain, and a hydroxyl group, which are widely distributed in plants and animals.

According to the invention herein, sterol compounds of natural origin are enriched only to a limited degree in sterol concentrates, with the proviso that these concentrates are to be immediately suitable for use in the fermentative conversion of sterols. The substances accompanying the sterols in the concentrates of the present invention do not interfere with the fermentative sterol transformation; on the contrary, they facilitate the performance of the fermentative transformation according to the invention. With regard to another aspect of the invention, the distillation residues of the industrial processing of vegetable and/or animal fats and/or oils, which are available in large quantities and were previously largely rejected as wastes, are to be used as starting material for the preparation of the novel sterol concentrates.

Surprisingly, it has been found that a novel, simple combination of procedural steps will produce, from fat-processing residues described herein, light-colored sterol concentrates that have sterol contents not exceeding 50 percent by weight and which can be used directly in the fermentation step, whereby the concentrates may be considered as a valuable starting material. According to the process of the invention, distillation residues from the processing of natural fats and/or oils are transesterified with a lower alkanol, the reaction product is subjected to molecular distillation, and a main fraction with a content of up to about 50 percent by weight of sterol compounds is separated thereby as a product of the process.

The amount of sterol contained in the distillate is from about 80 to 90% by weight of the sterol originally present in the residue to be worked up. Substances accompanying the sterols in the concentrates obtained according to the invention do not interfere with the fermentation and even make the concentrate easy to emulsify in the aqueous nutrient solution, which is desirable. The accompanying substances are fatty chemicals, which are also digestible for the microorganisms and are broken down during the fermentation, as are the normally added fatty chemical emulsifying agents. The very complex preparation of sterols in the pure form for the fermentation becomes superfluous with the use of the concentrates accoring to the invention.

Starting materials for the process according to the invention for the preparation of the light-colored sterol concentrates are distillation residues from the industrial cleavage of fat with production of fatty acids or distillation residues from the industrial transesterification of fats with production of fatty acid esters, for example, a fatty acid methyl ester. The starting fats include animal or vegetable fats or also the refining wastes, steam condensates, or fatty acids from soap stock.

In practice, the distillation residues normally are subjected to repeated cleavage or transesterification steps and are distilled to produce the highest degree of cleavage or transesterification possible. According to the invention, such repeatedly transesterified or repeatedly cleaved distillation residues are particularly suitable as starting material. The sterol compounds in the distillation residues preferred as starting material according to the invention are present in an enriched state in concentrations of from about 5 to 15 percent by weight, in the form of compounds of low volatility. They are present mainly in a form esterified with fatty acids. This is also the case with the sterols in the residues from the transesterification process since a reesterification of the previously released sterols takes place at the high temperatures of ester distillation.

These distillation residues are black substances which are partly liquid, partly solid at room temperature, but become molten below 50° C. The acid numbers are from about 20 to 80 for the residues from the cleavage and distillation of fatty acids, and the saponification numbers are from about 120 to 160. The acid numbers for transesterification residues from the methyl ester distillation are below 10, and the saponification numbers are from about 140 to 180. When the sterol content of such a residue is not sufficiently high, it can be raised to the desired level, within the scope of the invention, by cleavage with water at a high temperature of subsequent fatty acid distillation.

In a first step, which is important for the process according to the invention, the sterols in the selected distillation residues are set free by transesterification with lower alcohols in an autoclave. Suitable lower alcohols include the lower alkanols, preferably methanol, ethanol, propanol, and butanol. Methanol is of particular importance for this process step within the scope of the invention.

The ratio by weight of methanol to residue is preferably in the range from about 0.5:1 to 3:1 for this first process step, and working with ratios of about 1:1 is particularly suitable. This ratio is not subject to any true limitation in the upward direction, and thus the methanol may actually be used in any desired amount. The reaction itself is carried out in an autoclave. Suitable process temperatures are in the range from about 180° to 240° C., and the procedure is preferably performed at temperatures from about 200° to 220° C.

The transesterification is performed preferably under the influence of catalysts, especially basic catalysts. An alkali metal alcoholate, for example sodium methylate, or an alkali metal hydroxide, for example, potassium hydroxide, can be added as catalyst in amounts of, for example, from about 0.1 to 1, preferably up to 0.5, percent by weight, based on the amount of distillation residues used. However, a reaction takes place even without a catalyst, although at an appreciably slower rate in some cases. The reaction time usually is about 3 hours at 220° C., about 6 hours at 180° C.

Upon the completion of the reaction, the alkali metal catalyst is neutralized with dilute mineral acid, for example, dilute sulfuric acid, and then free alcohol and water are removed from the reaction mixture. This can be done simply by evaporation at temperatures of up to about 120° C. The residue is washed with water and dried at temperatures of up to about 120° C. to produce a mass that hardly moves, or a highly viscous liquid, at room temperature. If washing is difficult, the methanolic phase may also be separated, after the reaction of the distillation residue with methanol, by the addition of small amounts of water, further rinsing then being dispensed with.

In a second step of the process according to the invention, the transesterification product obtained is then subjected to molecular distillation under high vacuum. Known thin-layer evaporators are particularly suitable for this purpose, preferably thin-layer evaporators with an evaporation route from the evaporation surface of the thin film of substance to the condenser that is relatively short and has a distance of a few centimeters, for example. This can be achieved, for example, by the known vertical, coaxial arrangement of two cylindrical walls. The inner cylinder is formed as a cooling finger, while the heated inner side of the outer cylinder serves as an evaporation surface. The substance that flows down is distributed over the wall in the form of an even film by rotating wipers. The distillate collects at the cooled surface of the inner cylinder and runs down.

The transesterified residues with the released sterols are advantageously distilled at temperatures above about 200° C. and in a vacuum of less than about 0.5 mbar in the thin-layer evaporator. Suitable distillation conditions are temperatures in the range from about 200° to 300° C., preferably from about 220° to 280° C., and pressures of from about 0.01 to 0.5 mbar.

A predistillation prior to the production of the desired sterol concentrate fraction, in which a limited amount of a pre-run is separated, has been found advantageous in many instances. This predistillation can be carried out under a vacuum of from about 0.5 to 1 mbar. A pre-run distillate in the range from about 5 to 40 percent by weight, based on total weight of the distillation sample, is obtained in the temperature range of from about 120° to 200° C. This guarantees a high yield of sterol in the main distillation. It is technically possible to perform both distillations in two connected evaporators.

The pre-run distillate fraction consists mainly of methyl esters of fatty acids, and this fraction is either discarded or used for other purposes. The light-colored sterol concentrate desired according to the invention is then collected as the main distillate fraction.

The sterol concentrates are an additional aspect of the present invention. They advantageously consist primarily of up to about 50 percent by weight of sterol compounds and preferably of up to about 50 percent by weight of methyl esters of fatty acids, and comprise primarily methyl esters of hydroxylated and dihydroxylated fatty acids as well as partial glycerides in a very small quantity. This description of the concentrates is based upon the use of methanol in the transesterification step, and comparable quantities of analogous components would be present if a lower alkanol other than methanol were used. The resulting material, which is semisolid to solid at room temperature, has a golden yellow color, and its saponification number generally is in the range of from about 50 to 170, while the hydroxyl number is generally in the range of from about 40 to 150, preferably in the range of from about 40 to 120, in the unsaponified condition. This hydroxyl number of unsaponified distillate results partly from the sterol compounds and partly from the hydroxylated fatty acid methyl esters present in mixture with the former. This can be proven by saponification, isolation, and identification of the fatty acid part.

In preferred embodiments of the new sterol concentrates according to the invention, the content of sterol compounds is in the range of from about 10 to 45 percent by weight, preferably in the range of from about 15 to 40 percent by weight, based on the weight of this distillation fraction. Frequently the main run contains more than 20 percent by weight of sterols; however, a sterol content of up to about 20 percent by weight may also be suitable for the subsequent utilization of the concentrate.

The accompanying components present in the sterol concentrate in mixture with the sterols are not only not harmful for the subsequent use of the concentrate in the fermentative transformation of sterol, but, on the contrary, they prove to be surprisingly effective for the facilitation of the microbial conversion of the sterol compounds. The hydroxylated fatty acid esters present in the concentrate mixture provide the concentrate with very good emulsification characteristics. The proportion of hydroxylated esters may be further increased, if desired. This is advantageously achieved by the reduction of the amount of relatively volatile hydroxyl-free esters of fatty acid by distillation. The ability of the concentrate to emulsify in aqueous nutrient solutions is further improved, and the amount of sterol present in the concentrate is further increased in this manner. Naturally, a rise in the hydroxyl number is a consequence of this as well. However, even the simple thin-layer distillates with about 20% sterol compounds are basically substrates very well-suited for the transformation of sterol by fermentation.

In another embodiment of the present invention, the new sterol concentrates with only limited contents of sterol compounds obtained by the described process are used as starting material in the transformation of sterols by fermentation in which a controlled change in the chemical structure of the sterol compound is carried out by the action of certain microorganisms. The selected microorganisms are incubated and cultured in an aqueous nutrient medium in the normal manner for this purpose, and the sterol concentrates according to the invention are added to the fermenting liquid. The addition of these concentrates as the main, or even as the only, source of carbon may be desirable in this case. The fermentation usually is carried out under aerobic conditions, known to the art, such as are disclosed in W. Charney and H. L. Herzog, *Microbial Transformation of Steroids*, Academic Press, New York, 1967, incorporated herein by reference. Processes for the selective cleavage of side chains from steroid compounds by microbiological means are of particular importance today. A summarized review of these studies is found in Christoph K. A. Martin, "Microbial Cleavage of Sterol Side Chains," *Advanced Applied Microbiology*, 22, pages 29–58 (1977), incorporated herein by reference.

Of special significance is the use of the sterol concentrates according to the invention in the preparation of 17-C steroid-α-propionic acid compounds by selective side chain cleavage in side chain steroid substates as described especially in commonly assigned European patent application No. 79 101 036.6 and Austrian patent application No. 1709/79, as well as U.S. patent application Ser. No. 29,415, filed Apr. 12, 1979, which are incorporated herein by reference. The preparation of 3-oxo-pregna-4-ene-20-carboxylic acid ($\Delta^4$-BNC) and/or 3-oxo-pregna-1,4-diene-20-carboxylic acid ($\Delta^{1,4}$-BNC) from steroid substrates with longer substituents in the 17-C-position by fermentation is particularly made possible by this procedure. The microorganisms for this preferably inhibitor-free method are mutant strains that were obtained from certain selected wild strains and subsequent mutation and selection. Suitable defect mutant strain microorganisms for use in this connection are especially the strains ATCC 31385, ATCC 31456, ATCC 31457, ATCC 31459, ATCC 31460, DSM 4035, DSM 1437, DSM 1439, DSM 1442, DSM 1443, DSM 1444, and DSM 1445.

The following examples are intended to illustrate the invention and are not to be construed as limiting the invention thereto. All percentages are percent by weight.

EXAMPLES

EXAMPLE I (a) One thousand grams of residue from the processing of stearic acid were used, which residue was obtained after three cleavages and distillation. The residue had the following characteristic values:

Acid number: 19
Saponification number: 124
Hydroxyl number: 18
Iodine number: 65
Cholesterol content: 14%

After addition to the residue of 1000 gm of methanol and 16.7 gm of a 30% solution of methanolic sodium methylate, the resulting mixture was heated to 220° C. for 3 hours with agitation, in an autoclave. The autoclave product was neutralized with 45.3 gm of 10% aqueous sulfuric acid, 100 gm of water also being added. A lighter methanol phase separated after the addition. The heavier fat phase was separated and dried. The remainder of the methanol and water were distilled off, a water aspirator vacuum was applied towards the end of the distillation, and the pot temperature was raised to 120° C. The resulting mass comprised 960 gm of a black substance that was a solid at room temperature and had the following characteristics:

Acid number: 4
Saponification number: 110
Hydroxyl number: 69
Iodine number: 64

(b) Nine hundred grams of the black mass obtained, i.e., the tranesterification product, were distilled in two passages in a laboratory thin-layer evaporator (of the type of a molecular distillation; distance between cooling finger and wall with substance film: 1.7 cm). The first passage, i.e., pre-run, at about 120° C./approximately 1 mbar yielded 40 gm of liquid distillate that was almost free of cholesterol. A second distillation was carried out at 240° C./0.4 mbar, and 570 gm of golden yellow distillate were obtained, leaving 240 gm of black residue. This distillate contained 21.7% free cholesterol, as determined by chromatography. The analytical data for the distillate was as follows:

Acid number: 6.4
Saponification number: 127
Hydroxyl number: 79.4
Iodine number: 55.6

A glycerin analysis for free and bound glycerin yielded 0.16%. The fatty acid was isolated from a small sample by saponification. Its analytical data were as follows:
Acid number: 192
Hydroxyl number: 48

(c) A considerable shift in the relative amounts resulted from a drastic increase in the distillation temperatures:

A quantity of transesterification product prepared according to the procedure of Example I(a) was processed further analogously to Example I(b) except with significantly increased distillation temperatures. Thirty-eight percent of the transesterification product, which had a sterol content of 6,6%(as determined according to V. C. Mehlenbacher, *The Analysis of Fats and Oils,* 1960, page 592), was distilled at approximately 1 mbar and 200° C. The residue from the first distillation was distilled at 270° C./0.4 mbar. The resulting distillate fraction or concentrate had a 43% sterol content (as determined according to Mehlenbacher) and the following analytical characteristics:
Acid number: 3.6
Saponification number: 69.9
Hydroxyl number: 110.9
Iodine number: 57.7

The residue comprised 34% of the distillation starting material.

EXAMPLE II

One thousand grams of residue from the processing of acids from a mixture of soybean oil and sunflower oil obtained after two cleavages and distillation were employed. The residue obtained had the following characteristics:
Acid number: 71.5
Saponification number: 160
Hydroxyl number: 4.1
Iodine number: 102
Sterol content: 9.9%

The sterol component had the following composition:
Sitosterol: 60.9%
Campesterol: 21.1%
Stigmasterol: 15.4%
Cholesterol: 2.6%

After addition to the residue of 1000 gm of methanol and 16.7 gm of a 30% solution of methanolic sodium methylate, the resulting mixture was heated to 220° C. with agitation for 3 hours in an autoclave. The autoclave product was neutralized with 45.3 gm of 10% aqueous sulfuric acid, and then the methanol was distilled with agitation, until the pot temperature was 120° C. The residue was washed several times with water at 80° C. The remainder of the water and methanol were distilled off with agitation under water aspirator vacuum to a pot temperature of 120° C. Approximately 950 gm of a black substance that remained largely liquid at room temperature were obtained.

The black substance had the following characteristic values:
Acid number: 11.7
Saponification number: 145
Hydroxyl number: 58
Iodine number: 101

Nine hundred grams of the black transesterification product were distilled in a laboratory thin-layer evaporator (of the molecular distillation type; distance between cooling finger and wall with substance film; 1.7 cm) at about 220° C./0.4 mg Hg. The result was 570 gm of golden yellow distillate and 305 gm of black residue.

The distillate was determined to have a content, with digitonine, of 15.2% sterols and the following characteristic values:
Acid number: 8.1
Saponification number: 145.4
Hydroxyl number: 65.3
Iodine number: 96.4

EXAMPLE III

One thousand grams of product from the methanolic tallow transesterification after two cleavages and distillation which had a sterol content 9.1% (approximately 4% free sterol), were used. The product had the following characteristics:
Acid number: 3.3
Saponification number: 159
Hydroxyl number: 40.5
Iodine number: 61.5

The residue was transesterified as described in Example II and distilled as described in Example I(b). The distillation yielded 220 gm of pre-run distillate and 580 gm of main fraction distillate. The main fraction contained 12.8% free sterol and had the following characteristics:
Acid number: 4
Saponification number: 161
Hydroxyl number: 47.5
Iodine number: 64

EXAMPLE IV

One thousand grams of residue from the methanolic tallow transesterification after two transesterifications and distillations, which had a sterol content of 7.4% (approximately 4% free sterol), were used. The residue had the following characteristics:
Acid number: 2
Saponification number: 165
Hydroxyl number: 16
Iodine number: 60

The residue was first subjected to ester cleavage with 2,000 gm of water for 4 hours at 220° in an autoclave. The fatty phase was distilled under vacuum, at approximately 0.1 mbar. The distillation was interrupted when the pot temperature reached 210° C. The distillation residue was 460 gm and had a sterol content of 14.6%.

The 460 gm residue were transesterified as described in Example II. The product obtained had the following analytical data:
Acid number: 15
Saponification number: 131
Hydroxyl number: 56
Iodine number: 70

The transesterification product was distilled in a thin-layer evaporator such as is described in Example I(b). A pre-run distillate of 50 gm and a light yellow main fraction of 270 gm, which slowly solidified below 60° C., were obtained. The main fraction contained 21% free cholesterol and that the following analytical characteristics:
Acid number: 9.5
Saponification number: 132
Hydroxyl number: 63
Iodine number: 59

The analysis for free and bound glycerin yielded 0.05%.

EXAMPLE V

One thousand grams of residue from fish oil after two cleavages and distillation, were used. The residue contained 7.5% cholesterol and had the following characteristics:
  Acid number: 72
  Saponification number: 161
  Hydroxyl number: 19
  Iodine number: 152

This residue was transesterified with 1,000 gm of methanol, without catalyst, for 3 hours at 220° C. The methanol was evaporated from the transesterification product without a precedent washing. The evaporation residue was distilled in a thin-layer evaporator at 240° C./0.1 mbar, and 696 gm of distillate were obtained. The distillate contained 9.3% free sterol and had the following characteristics:
  Acid number: 1.8
  Saponification number: 156
  Hydroxyl number: 59.5
  Iodine number: 134

EXAMPLE VI

The sterol concentrates of Examples I, II, IV, and V were fermented with and without the use of the emulsifying agent BRIJ 35 (polyoxyethylene monolauryl ether, from Serva, Heidelberg) to obtain 20-carboxyl-1,4-pergnadien-3-one ($\Delta^{1,4}$-BNC). Microorganisms of strain ATCC 31385 were used for this purpose.

The workup was performed as follows:
Preculture:
  The strain Chol 73-Mll, corynebacterium spec. (ATCC 31385) was first precultured in 100 ml of sterile nutrient broth (1.56% peptone, 0.28% yeast extract, 0.56% NaCl, 0.1% D (+)-glucose, pH 7.2) at 30° C. for 48 hours on a shaking incubator (rate: 140 rpm).
Main culture:
  Two percent by volume of the 48-hour preculture were inoculated in 100 ml of sterile nutrient solution (500 ml Erlenmeyer flask with 4 baffles) of the following composition: 0.05 M K—Na—PO$_4$— buffer (pH 7.2), 0.8% peptone, 0.9% yeast extract, 0.3% D(+)-glucose. After incubation for 42 to 48 hours at 30° C. (cultural conditions as above), 0.1% emulsifying agent and/or 0.1% sterol substrate were added. Prior to the main culture, each sterilized substrate suspension was homogenized by ultrasound.

The batches were harvested after 144 hours of culture and samples were taken, adjusted to pH 2.0, extracted 1:1 with ethyl acetate, and analyzed by quantitative thin-layer chromatography. The data for the individual batches is set forth in the following table:

TABLE

| Substrate (adjusted to 0.1% sterol) | Emulsifying agent (0.1% BRIJ 35) | Yield of BNC (%) |
|---|---|---|
| Example I(b) | + | 84 |
| Example I(b) | − | 85 |
| Example IV | + | 77 |
| Example IV | − | 47 |
| Example V | + | 73 |
| Example V | − | 67 |
| Cholesterol | + | 82 |
| Cholesterol | − | 56 |
| Example II | + | 62 |
| Example II | − | 26 |
| β-sitosterol | + | 30–40 |

+ with emulsifying agent
− without emulsifying agent

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the preparation of a concentrate containing sterol compounds of natural origin, which concentrate is suitable as a starting material for the transformation of sterol compounds by fermentation, which comprises the steps of:
   (a) transesterifying sterol-containing distillation residues from the processing of natural fats and/or oils with a lower alcohol; and
   (b) subjecting the product of step (a) to molecular distillation to produce a main fraction having a content of up to about 50 percent by weight of sterol compounds.

2. The process of claim 1, wherein the distillation residues in step (a) have a sterol content of from about 5 to 15 percent by weight.

3. The process of claims 1 or 2, wherein the distillation residues have resulted from multiple cleavage of fats.

4. The process of claim 1, 2, or 3, wherein the transesterification of the distillation residues of step (a) is with methanol.

5. The process of claim 1, wherein from 5 to 40% by weight of the product of step (a) is removed by molecular distillation at a lower temperature and less vacuum prior to molecular distillation in step (b) to produce a main fraction.

6. The process of claim 1 or 5, wherein the molecular distillation is performed in a thin-layer evaporator.

7. The process of claim 5, wherein the molecular distillation is performed in the temperature range of from about 120° to 200° C. and at a vacuum of from about 0.5 to 1 mbar.

8. The process of claim 1, wherein the molecular distillation of step (b) is performed at temperatures greater than about 200° C. and at a vacuum of less than about 0.5 mbar.

9. The process of claim 8, wherein the molecular distillation of step (b) is performed at temperatures in the range of from about 200° to 300° C. and at a vacuum of from about 0.01 to 0.5 mbar.

10. The process of claim 9, wherein the molecular distillation of step (b) is performed at temperatures in the range of from about 220° to 280° C.

11. Sterol concentrates obtained by distillation of residues of fat processing after transesterification with methanol and having a saponification number of 50 to 170 and an OH-number (unsaponified) of 40 to 150, comprising up to about 50 percent by weight of sterol compounds, up to about 50 percent by weight of methyl esters of hydroxylated and non-hydroxylated, fatty acids and small amounts of partial glycerides.

12. The process of claim 1, wherein the distillation residues in step (a) contain animal and/or plant sterols.

13. The process of claim 12, wherein the sterols are selected from the group consisting of sitosterol, campesterol, stigmasterol, cholesterol, and mixtures of two or more thereof.

14. The process of claim 13, wherein the residues contain cholesterol.

15. Sterol concentrates prepared according to claim 1, said concentrates having a saponification number of from about 50 to 170 and an OH-number (unsaponified) of from about 40 to 150 and comprising up to about 50 percent by weight of sterol compounds.

16. The concentrates of claim 11 or 15, wherein the sterol compounds are animal and/or plant sterols.

17. The concentrates of claim 16, wherein the sterol compounds are selected from the group consisting of sitosterol, campesterol, stigmasterol, cholesterol, and mixtures of two or more thereof.

18. The concentrates of claim 17, wherein the sterol compounds are cholesterol.

* * * * *